United States Patent
Fragouli et al.

(10) Patent No.: US 9,676,914 B2
(45) Date of Patent: Jun. 13, 2017

(54) PROCESS FOR PRODUCING POLYMER FOAMS

(71) Applicant: Fondazione Istituto Italiano de Tecnologia, Genoa (IT)

(72) Inventors: Despina Fragouli, Genoa (IT); Elisa Mele, Castrignano dei Greci (IT); Athanasia Athanasiou, Ceranesi (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 54 days.

(21) Appl. No.: 14/651,764

(22) PCT Filed: Dec. 23, 2013

(86) PCT No.: PCT/IB2013/061278
§ 371 (c)(1),
(2) Date: Jun. 12, 2015

(87) PCT Pub. No.: WO2014/102708
PCT Pub. Date: Jul. 3, 2014

(65) Prior Publication Data
US 2015/0315353 A1    Nov. 5, 2015

(30) Foreign Application Priority Data
Dec. 28, 2012   (IT) .............................. TO2012A1159

(51) Int. Cl.
| | |
|---|---|
| *C08J 9/26* | (2006.01) |
| *C08J 9/36* | (2006.01) |
| *C08J 9/00* | (2006.01) |
| *A61L 27/48* | (2006.01) |
| *A61L 27/56* | (2006.01) |

(52) U.S. Cl.
CPC ................ *C08J 9/26* (2013.01); *A61L 27/48* (2013.01); *A61L 27/56* (2013.01); *C08J 9/0061* (2013.01); *C08J 9/36* (2013.01); *A61L 2400/08* (2013.01); *C08J 2201/046* (2013.01); *C08J 2201/0464* (2013.01); *C08J 2205/022* (2013.01); *C08J 2205/05* (2013.01); *C08J 2333/06* (2013.01); *C08J 2375/04* (2013.01); *C08J 2383/04* (2013.01); *C08J 2389/00* (2013.01); *C08J 2400/14* (2013.01); *C08J 2401/02* (2013.01); *C08J 2405/04* (2013.01); *C08J 2405/08* (2013.01); *C08J 2431/04* (2013.01); *C08J 2433/26* (2013.01); *C08J 2477/06* (2013.01)

(58) Field of Classification Search
CPC ...... A61L 27/48; A61L 27/56; A61L 2400/08; C08J 9/0061; C08J 9/26; C08J 9/36; C08J 2201/046; C08J 2201/0464; C08J 2205/022; C08J 2205/05; C08J 2333/06; C08J 2375/04; C08J 2383/04; C08J 2389/00; C08J 2400/14; C08J 2401/02; C08J 2431/04; C08J 2433/26; C08J 2477/06
See application file for complete search history.

(56) References Cited

U.S. PATENT DOCUMENTS

| | | | |
|---|---|---|---|
| 2008/0206308 A1* | 8/2008 | Jabbari | ................ A61L 27/48 424/426 |
| 2013/0184835 A1* | 7/2013 | Ferrari | ................ A61L 27/446 623/23.61 |
| 2014/0079752 A1* | 3/2014 | Huebsch | ................ A61L 27/26 424/422 |

FOREIGN PATENT DOCUMENTS

| | | | |
|---|---|---|---|
| WO | WO2005020849 | * | 3/2005 |
| WO | WO2010046084 | * | 4/2010 |
| WO | WO2012005783 | * | 1/2012 |

* cited by examiner

*Primary Examiner* — Irina S Zemel
(74) *Attorney, Agent, or Firm* — MacMillan, Sobanski & Todd, LLC

(57) ABSTRACT

Process for the production of a polymer foam with use of hydrogel pearls as porosity generating template, comprising the steps of:—providing a matrix of polymer or prepolymer in viscous state including, as a dispersed phase, hydrogel pearls, where said pearls are dispersed in said matrix so as to generate intercommunicating cells,—causing the solidification of the matrix of polymer or prepolymer to obtain said polymer foam including said hydrogel pearls, characterised in that it comprises the operation of subjecting the thus obtained foam to conditions which cause the dehydration of said hydrogel pearls so as to obtain a reduction of volume of said pearls and—removing the dehydrated pearls by immersion in water of the polymer foam or by exposure of the foam to a flow of pressurized gas or water.

11 Claims, No Drawings

PROCESS FOR PRODUCING POLYMER FOAMS

This is a national stage application filed under 35 U.S.C. §371 of international application PCT/IB2013/061278, filed under the authority of the Patent Cooperation Treaty on Dec. 28, 2013, published; which claims the benefit of Patent Application No. TO2012A001159, filed on Dec. 28, 2012. The entire disclosures of all the aforementioned applications are expressly incorporated herein by reference for all purposes.

The present invention relates to a process for producing expanded polymeric materials or articles or polymer foams, by using hydrogel pearls as a porosity-generating template.

The production of polymer foams by using hydrogel pearls as porogen is known and constitutes a valid alternative to conventional methods for producing expanded articles which use physical or chemical expanders, particularly for the production of porous supports (scaffolds) for use in the medical field.

WO 2010/025219 describes the production of expanded polymers, having various antimicrobial properties, which contain alginate pearls with antimicrobial agents as subsequent sacrificial porosity generator. The use of pearls with different sizes makes it possible to modulate the density of the expanded material used. The pearls are removed from the expanded material by dissolution.

Hamasaki S. et al. in Materials Science and Engineering C. 28 (2008), 1250-1254, describe the production of highly porous and flexible keratin foams which contain dehydrated calcium alginate pearls via the "freeze-drying" and lyophilization technique; following the formation of the foam, the pearls are removed via a lyophilization technique.

Tomei A. A. et al. in Biotechnology and Bioengeneering, Vol. 103, n. 1, May 1, 2009, describe the production of polyurethane polymer foams, by using dehydrated calcium alginate pearls; following solidification of the polymer, the pearls are removed by dissolution in citric acid solution.

EP 2 179 751 A1 describes a process for producing a crosslinked macroporous polymer material in which hydrogel pearls are dispersed in a polymerizable monomer; after polymerization of the monomer, the solid pearls are liquefied and removed from the polymer matrix.

One aim of the present invention is to provide an alternative process for producing polymer foams, which, by using hydrogel pearls as porogen, simplifies the operating procedure, facilitating the removal of the polymer foam thus obtained from the hydrogel pearls.

Another aim of the invention is to provide an alternative process for obtaining expanded materials, particularly functionalized polymer foams, i.e. foams containing active agents, for instance functional macromolecules, located on the surface of the walls of the cells constituting the expanded material.

These aims are achieved by means of a process having the characteristics defined in the following claims, which constitute an integral part of the present description.

In the process according to the invention, the production of the polymer foams is performed by mixing a polymer or prepolymer solution in the viscous liquid form with pearls of a hydrogel which may consist of natural or synthetic materials, preferably biocompatible materials.

A wide range of materials may be used for producing hydrogel pearls, for instance alginate, cellulose, polyvinyl acetate (PVA), chitosan, agarose, polyacrylamide (PAA) or poly-N-isopropylamide (poly(NIPAAm)).

The techniques for producing hydrogel pearls are known per se.

Alginate pearls (which constitute a preferred hydrogel for the purposes of the invention) may be obtained by slowly adding dropwise a sodium alginate/water solution into an aqueous solution containing calcium chloride, calcium lactate or another calcium salt. Exchange of the sodium ions with the calcium gives rise to gelatinization and to the formation of calcium alginate pearls, which contain a specific amount of water trapped therein.

Cellulose pearls may be obtained, for example, by adding dropwise, into deionized water, a solution of microcrystalline cellulose and N,N-dimethylacetamide/lithium chloride, as ionic liquid. The solvent exchange between the water and the ionic liquid results in the formation of cellulose hydrogel pearls.

The initial size of the pearls may range from 1-2 mm to a few tenths of a micron, for instance 0.1 µm. In general, the sizes of the pearls depends on the method used for forming them and may thus be regulated according to the requirements. To obtain larger-sized pearls, within the ranges mentioned above, use may be made of a simple needle or a pipette for the purpose of adding the sodium alginate or the cellulose dropwise into the solution of calcium salt or into the solution of ionic liquid, respectively.

Small-sized micropearls, within the range indicated above, may be obtained, for example, by using microfluidic drop generators, for instance T, H or Y junctions, flow-focusing devices or passive break-up configurations.

Sodium alginate or cellulose emulsions in an oily phase may be formed at the junction between microchannels, in a microfluidic device, in which the flow of the dispersed phase (for example sodium alginate or cellulose) becomes unstable and fragments periodically to give rise to droplets in the continuous phase constituted by the oily liquid.

The alginate or cellulose drops are then collected in or transferred into the calcium-ion solution or the aqueous ionic solution and, after uniform gelatinization, water-insoluble calcium alginate or cellulose microspheres are obtained.

The size of the drops and consequently the size of the pearls are mainly controlled by the flow rate of the oil constituting the vehicle and by the flow rate of the material phase constituting the hydrogel, in the microfluidic device used; micropearls with a diameter in the range from 900 µm to 10 µm may be obtained.

It is understood that the invention is not limited to particular methods for generating pearls, with a monodisperse or polydisperse size distribution, within the range of micrometric or sub-micrometric sizes; alternative methods include mixing or sonication processes or electrodynamic methods.

The process according to the invention applies to the production of expanded polymers using a wide range of polymers, which include natural or synthetic materials or combinations thereof (including composite systems) with elastomeric, thermoplastic or thermosetting properties.

The preferred materials include, for example, polydimethylsiloxane (PDMS), natural rubbers, gelatin, acrylates and polyurethanes. The polymer foams to which the invention relates are characterized by a structure with interconnected pores, i.e. intercommunicating open cells.

To obtain such a structure, a preferred embodiment envisages the operation of placing the hydrogel pearls in a given volume or container, such that the pearls are packed together in mutual contact. The shape of the internal volume of the container may correspond to the shape of the foam article that it is intended to obtain.

Next, the viscous solution of polymer or prepolymer is poured into the container so as to cover the pearls packed therein, such that the polymer or prepolymer solution constitutes the matrix in which are dispersed the hydrogel pearls in contact with each other.

The subsequent operation includes solidification of the polymer or polymerization of the prepolymer, which is naturally performed as a function of the specific characteristics of the material used. For example, the solidification of a polymer solution may be obtained simply by evaporating off the solvent, or, in the case of use of prepolymer solutions, the solidification is obtained by crosslinking.

The subsequent phase of the production process involves the operation of subjecting the polymer foam, obtained after the solidification, including the hydrogel pearls as a dispersed phase, to conditions which bring about the distribution of the hydrogel pearls, with a consequent substantial reduction of their volume.

Although the dehydration may also be performed by maintaining at room temperature and pressure, it is preferable to use accelerated dehydration, by maintaining the foams obtained under controlled vacuum conditions (for example at a pressure from 25 mmHg Torr) to <760 mmHg and at a temperature equal to or slightly higher than 50° C. (for example 50-60° C.). These conditions bring about release of the water from the pearls and a consequent volume reduction, with formation of interconnected pores.

The dehydrated pearls may be readily extracted, for example by placing the foam thus obtained in a bath of water, using compressed air or a stream of water or inert gas; the size of the pores corresponds to the sizes of the pearls initially used.

The dehydration kinetics of the pearls depends on the specific hydrogel used, where appropriate, and on the initial size of the pearls; the dehydration process is faster the smaller the initial size of the pearls (for example about 50 minutes for pearls about 1-2 mm in size, and 15 minutes for pearls about 300 μm in size at room temperature and under atmospheric conditions).

In an alternative embodiment, the polymer foams may be obtained by in situ generation of hydrogel pearls in a viscous polymer matrix, avoiding the stage of polymerization of the hydrogel in ionic solutions, by using fluidic or microfluidic devices (such as the above-mentioned devices with T, H or Y junctions) fed with a stream of polymer or prepolymer solution and with a stream of hydrogel, intended to constitute the dispersed phase.

For example, in the case of alginate, it is possible to obtain the formation of drops of sodium alginate in continuous flow in a polymer (for example PDMS) in a microfluidic device and then to feed the polymer solution, including the drops of hydrogel as dispersed phase into a container for the production of the foam. The flows of polymer solution and of hydrogel may be regulated to obtain a foam structure with interconnected pores. The pearls thus obtained are then assembled and packed in the container and, after solidification of the polymer or prepolymer, the final foam is obtained by directly dissolving in water the water-soluble alginate contained in the cavities of the foam.

According to another preferred embodiment, directed towards the production of polymer foams with functional characteristics, the process involves the encapsulation in the hydrogel pearls of functional substances or agents or precursor compounds of functional molecules or agents, which preferably have high chemical affinity with the polymer material intended to be used for the formation of the foam. Such functional molecules and/or precursors of nanoparticles of diverse nature (for instance Au, Ag or Pt) may exhibit, for example, pharmaceutical or antibacterial activity, or a bind to various macromolecules or heavy metals or oily substances or substances that are environmentally hazardous.

Functional molecules or precursors may be encapsulated in the hydrogel pearls by addition to the solution in which the pearls are formed, for example to the solution of calcium ions used for the production of calcium alginate pearls; alternatively, the abovementioned functional substances or precursors thereof may be encapsulated in the pearls also in the case, mentioned previously, in which the dispersion of pearls is obtained by in situ generation in the polymer or prepolymer in the viscous state.

It is observed that the dehydration or dissolution of the hydrogel pearls, within the solidified polymer foam, is such that the functional substances or precursors thereof are chemically or physically adsorbed and immobilized on the cell walls of the foam, making it possible to obtain functional foams in which the functional activity is strongly localized only on the inner surface of the cells or pores of the foam, generating efficient active sites for subsequent reactions or processes.

In a preferred embodiment, precursor compounds of metals may be used, for instance acids or salts of Au, Ag, Zn, Cu or Pt that are capable of being chemically reduced, to generate the corresponding metal, via functional groups present in the polymer material.

This embodiment is particularly advantageous, in combination with the use of polymers containing functional groups with reducing action, particularly PDMS.

For example, precursor salts or acids of Au, Ag, Zn, Cu or Pt may be chemically reduced by the presence of Si—H functional groups present in the PDMS polymer foams, resulting in the formation of metal nanoparticles that are chemically bonded and trapped on the surface of the foam cells.

In the case of foams which do not contain functional groups suitable for bringing about the chemical reduction of the precursor, it is possible to use other reduction processes, induced by external stimuli, for instance light irradiation or heat treatment.

It is understood, as already indicated, that other functional molecules (for instance proteins, DNA, nanoparticles) may be trapped in the hydrogel pearls.

The process enables the localization of compounds with functional activity in localized areas, avoiding the need to load the entire polymer matrix with such molecules and reducing the final cost.

EXAMPLE 1

Production of Calcium Alginate Pearls Containing Chloroauric Acid

For the purposes of producing a polymer foam characterized by gold nanocomposite pores, alginate pearls containing the gold precursor were first prepared. In particular, pearls 1-2 mm in diameter are formed by adding dropwise an aqueous solution of sodium alginate (3% by weight) to an aqueous solution containing calcium chloride (10% by weight) which contains 1 mg/ml of chloroauric acid. After gelation thereof, the pearls trap the gold precursor. This precursor, during the foam formation phase, is released and chemically reduced by the polymer matrix constituting the foam.

EXAMPLE 2

Preparation of a PDMS Foam Using the Pearls of Example 1

The pearls produced are placed in a container, into which is subsequently added a high-viscosity liquid solution of PDMS, consisting of the prepolymer and of a curing agent in a 10:1 weight ratio. The system is then left to polymerize at room temperature and atmospheric pressure for 1-2 days. After polymerization of the matrix, the system is removed from the container and left for 3 hours under gentle vacuum and at a temperature of 50° C. This brings about release of the precursor solution from the PDMS alginate pearls and their subsequent chemical reduction with the formation of gold nanoparticles, due to the presence of the Si—H groups of the polymerized matrix. Next, the PDMS-pearl system is placed in a bath of water or under a flow of water in order to remove the dehydrated pearls, leaving pores in the polymer matrix and consequently bringing about the formation of the foam.

For comparative purposes, experiments were performed to dissolve the calcium alginate pearls using various acidic and basic solutions, including citric acid. However, it was not possible to obtain dissolution of the alginate, but only swelling of the pearls.

For the proposed method, the most important aspect is the dehydration of the pearls in order to obtain release of the substances of interest in the polymer matrix. The use of a flow of water or of air rather than a chemical solution is the simplest method, is ecological and a cheap way for removing the dehydrated pearls from the foam. In addition, the use of acidic solutions might bring about changes to the metal nanoparticles formed with a consequent loss of the performance qualities and functionalities of the foam produced.

The polymer foams or nanocomposite polymer foams that are the subject of the invention find application in the following technical fields:
1. biological application, in which the foams obtained may be used as scaffolds, artificial implants or for the immobilization of cells, functional proteins or other macromolecules. Each single cell of the foam can act as a reaction chamber for biological reactions, multiplex assays and cellular encapsulation. In addition, it is possible to produce integrated microdevices from the polymer foams to guide the cell growth, since the exchange of nutrients and gases is promoted by the porosity of the foam. Some materials proposed for such applications may comprise elastomeric foams, biodegradable foams obtained from natural polymers, for instance starch, expanded natural rubber bearing nanocomposite pores or pores with functional ligands. Some of these foams may have particular optical properties, such as transparency, which is of interest for the optical revelation of biological events that take place inside or on the surface of the foam;
2. for chemical analysis of waters or other liquids. In this case, the specific functionalization of predefined cells of the foam may induce the explicit binding of chemical substances thereon, facilitating the subsequent analysis;
3. for environmental applications, for example for water purification. The polymer foams may have functional nanocomposite pores, on the walls of which are anchored metal nanoparticles, such as Au, Pt and Ag, which act as filters, trapping toxic and harmful substances present in the water passing therethrough. In addition, these types of foams may be used for water-oil separations due to the functionalization appropriateness of their mass and surface. For the purpose of obtaining this result, the use of Teflon or other highly hydrophobic polymer particles on the surface or of iron oxide or of other oleophilic nanoparticles in the bulk may transform the foams into superhydrophobic oil-absorbing foams, preventing water from penetrating, but efficiently absorbing oil. Iron oxide or other magnetic oleophilic nanoparticles make the foams magnetic, and as such a weak magnet can push the floating foams toward the areas polluted with oil/petroleum, where the foams can act efficiently to bring about a cleaning action, by absorbing the oil/petroleum. Such a treatment may also be extended to other types of foams (for example polyurethane foams);
4. purification of oily substances such as glycerol, petroleum, etc., separating these substances from water, excess moisture, solvents, etc.;
5. nanocomposite foams with cells mainly functionalized with metal particles or emitters or with emitting dyes may be used for the production of miniaturised elements that are useful in the optical field and in the field of plasmonics.

The invention claimed is:
1. Process for the production of a polymeric foam with use of hydrogel pearls as porosity generating template, comprising the steps of:
providing a matrix of polymer or prepolymer in viscous state including, as a dispersed phase, hydrogel pearls, where said hydrogel pearls are dispersed in said matrix so as to generate intercommunicating cells,
causing the solidification of the matrix of polymer or prepolymer to obtain said polymeric foam including said hydrogel pearls by subjecting the thus obtained polymeric foam to conditions which cause dehydration of said hydrogel pearls so as to obtain a reduction of volume of said hydrogel pearls and
removing the dehydrated pearls by immersion in water of the polymeric foam or by exposure of the polymeric foam to a flow of pressurised gas.
2. Process according to claim 1, characterised in that said hydrogel pearl is selected from the group comprising alginate, cellulose, polyvinyl acetate, chitosan, agarose, polyacrylamide and poly-N-isopropylamide.
3. Process according to claim 1, characterised in that said polymer or prepolymer is selected from the group which comprises elastomeric polymers, thermoplastic and thermosetting materials, polydimethylsiloxane, gelatin, acrylates or polyurethanes.
4. Process according to claim 1, characterised in that the dehydration of the hydrogel pearls is obtained by subjecting the foam to temperature conditions of above 50° C. and/or subatmospheric pressure.
5. Process according to claim 1, characterised in that said polymer or prepolymer matrix, including said hyrdogel pearls as a dispersed phase, is obtained by packing the hydrogel pearls in conditions of mutual contact in a predetermined volume and feeding said viscous liquid polymer or prepolymer solution into said volume, so as to form said matrix.
6. Process according to claim 1, characterised in that said hydrogel pearls are generated in situ, in said matrix of said viscous liquid polymer or prepolymer with the use of a fluidic device comprising a T, H or Y junction, in which a stream of polymer or prepolymer, and a stream of hydrogel pearls are set in contact.

7. Process according to claim 1, characterised in that said hydrogel pearls comprise substances, macromolecules and/or precursor compounds of nanoparticles which play a functional activity, particularly therapeutic activity, of chemical-physical processes, of biological, chemical and environmental testing, of water purification, oil and other liquids.

8. Process according to claim 7, characterised in that said precursor compounds include salts or acids of a metal.

9. Process according to claim 8, characterised in that said precursor comprises a salt or an acid of a metal selected from gold, silver, zinc, copper or platinum.

10. Process according to claim 9, characterised in that the polymer is polydimethylsiloxane.

11. Process according to claim 9, wherein the process further comprises a stage of chemical reduction of said metal salt or acid made following solidification of the foam.

\* \* \* \* \*